Oct. 5, 1971 C. PEARLSTEIN Plant Pat. 3,066
AZALEA PLANT
Filed Feb. 17, 1969
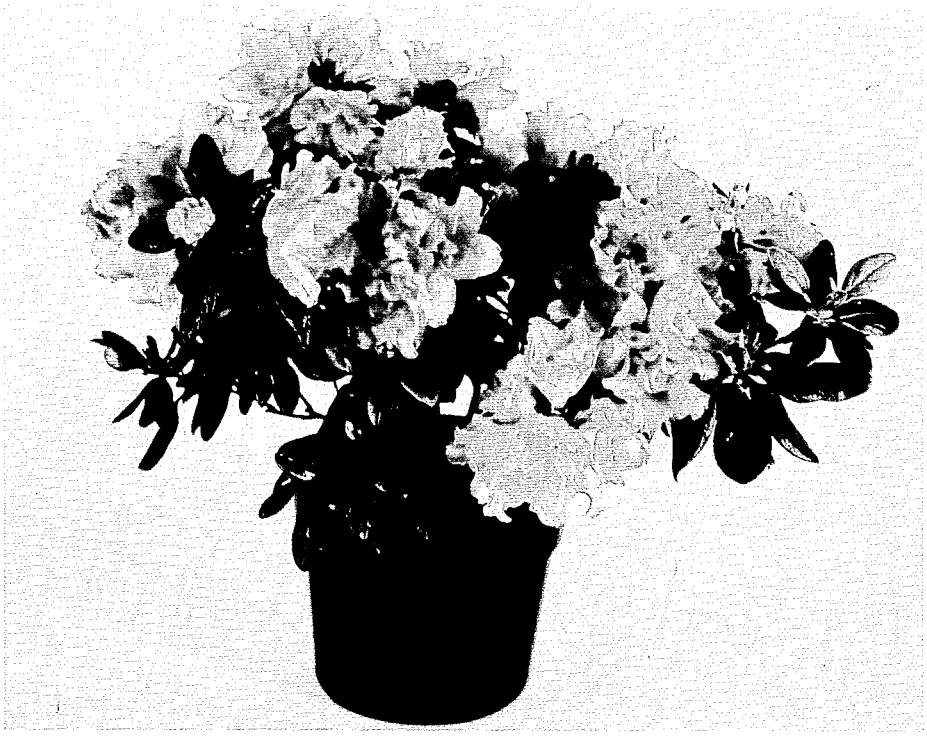

United States Patent Office

Plant Pat. 3,066
Patented Oct. 5, 1971

3,066

AZALEA PLANT

Carl Pearlstein, San Francisco, Calif., assignor to Nurserymen's Exchange, Inc.

Filed Feb. 17, 1969, Ser. No. 800,009
Int. Cl. A01h 5/00
U.S. Cl. Plt.—57 1 Claim The invention relates to a new and distinct variety of azalea plant of the Belgian Indica class, discovered by me in a cultivated area, namely in the greenhouses of Nurserymen's Exchange at Half Moon Bay, Calif. My new azalea plant is a sport of "Improved Red Wing," Ser. No. 692,610, filed Dec. 21, 1967, now Plant Pat. 2,918.

This sport was selected and propagated because of its novel color, and its increased doubleness over the parent. These characteristics in combination with the superior vegetative characteristics of the parent make this variety novel and superior to other Belgian Indica varieties in its color class. These characteristics which are outstanding in the new variety distinguish it from its parent as well as from all other varieties of which I am aware. My new variety is primarily characterized by: its vegetative similarity to "Improved Red Wing," above identified, of which it is a sport and by its China Rose color (HCC 024/1), its greater tendency to produce double bloom and its tendency to have fasciated, multiple styles. The foliage while similar in form to Plant Patent 2,918, is darker when mature.

Asexual reproduction of my new variety by cuttings, through a series of propagations at the greenhouses of Nurserymen's Exchange at Half Moon Bay, Calif., shows that all characteristics of the variety come true to form through succeeding propagations. The accompanying photograph illustrates the primary characteristics of my new variety as nearly true as is reasonably possible to make them with presently available techniques. The color reference cited is that of the Horticultural Colour Charts of the Royal Horticultural Society.

The following botanical description is based upon observations of plants in clay pots grown under greenhouse conditions at Half Moon Bay, Calif.

A new variety of Florists Azalea of the Belgian Indica class characterized by its vegetative similarity to "Improved Red Wing" of which it a somatic mutation, but differing from the parent variety in color being a bright China Rose (HCC 024/1) in general color tonality and also by certain minor variations of flower, foliage and tomentum, most particularly in having a greater tendency to doubleness of the bloom, by producing a high percentage of fasciated multiple styles, by having fewer prominent secondary foliar veins, and by strigae that are less dense and lighter colored though often quite black. The "Improved Red Wing" was in full flower and the pink sport of the present invention in about ⅕ full bloom, ⅗ well colored buds and ⅕ tight buds on Dec. 15, 1968. A comparison of the habit of growth of the two varieties was impaired because the plants had been wired, altering the natural growth habit. However, the branches of the sport seemed to be more ascending than those of the parent variety.

Having thus disclosed my invention, I claim:

1. A new and distinct variety of azalea plant of the Belgian Indica class substantially as herein shown and described primarily characterized by its general similarity to "Improved Red Wing" of which it a sport and by its China Rose color (HCC 024/1), its greater tendency to produce double bloom and its tendency to have fasciated, multiple styles.

No references cited.

ROBERT E. BAGWILL, Primary Examiner